US011660433B2

United States Patent
Li et al.

(10) Patent No.: US 11,660,433 B2
(45) Date of Patent: May 30, 2023

(54) PRESSURE RELIEF FOR A CATHETER BALLOON DEVICE

(71) Applicant: Medtronic Xomed, Inc., Jacksonville, FL (US)

(72) Inventors: Wenjeng Li, Saint Johns, FL (US); David J. Little, Ponte Vedra, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 379 days.

(21) Appl. No.: 16/929,245

(22) Filed: Jul. 15, 2020

(65) Prior Publication Data

US 2020/0338326 A1 Oct. 29, 2020

Related U.S. Application Data (63) Continuation of application No. 15/715,249, filed on Sep. 26, 2017, now Pat. No. 10,737,077, which is a
(Continued)

(51) Int. Cl.
*A61M 29/02* (2006.01)
*A61M 25/10* (2013.01)
(Continued)

(52) U.S. Cl.
CPC ...... *A61M 29/02* (2013.01); *A61M 25/10182* (2013.11); *A61M 25/10186* (2013.11);
(Continued)

(58) Field of Classification Search
CPC ...... A61M 25/10187; A61M 25/10182; A61M 5/14; A61M 2210/0618;
(Continued)

(56) References Cited

U.S. PATENT DOCUMENTS

| 4,059,017 A | 11/1977 | Settlemyer et al. |
| 4,246,899 A * | 1/1981 | Loseff ............... A61M 1/77 604/97.02 |

(Continued)

FOREIGN PATENT DOCUMENTS

| EP | 2060293 | 5/2009 |
| EP | 2236168 | 10/2010 |

(Continued)

OTHER PUBLICATIONS

International Search Report and Written Opinion, PCT/US2014/012974, dated May 21, 2014, 14 pages.
(Continued)

*Primary Examiner* — Julian W Woo
(74) *Attorney, Agent, or Firm* — Carter, DeLuca & Farrell LLP (57) ABSTRACT

A method of limiting an inflation system pressure for dilating a region of a patient's nasal sinus passageways. The method includes grasping an inflation device. The inflation device includes a syringe including a plunger slidably disposed within a barrel, a connector for fluidly connecting an outlet of the syringe with a surgical instrument balloon, and a mechanical pressure indicator associated with the syringe, the mechanical pressure indicator including a housing and an indicator body disposed within the housing. The method also includes delivering the surgical instrument balloon to a patient's paranasal sinus target area, operating the plunger within the barrel of the syringe to deliver pressurized fluid to the surgical instrument balloon, and transitioning the indicator body to extend outside of the housing when a predetermined inflation pressure of the surgical instrument balloon is reached.

15 Claims, 10 Drawing Sheets

Related U.S. Application Data continuation of application No. 14/486,033, filed on Sep. 15, 2014, now Pat. No. 9,770,577.

(51) Int. Cl.

| | |
|---|---|
| *A61B 17/00* | (2006.01) |
| *A61B 17/22* | (2006.01) |
| *A61B 90/00* | (2016.01) |
| *A61B 17/24* | (2006.01) |
| *A61M 5/14* | (2006.01) |

(52) U.S. Cl.
CPC ........ *A61M 25/10187* (2013.11); *A61B 17/24* (2013.01); *A61B 2017/00557* (2013.01); *A61B 2017/22051* (2013.01); *A61B 2090/032* (2016.02); *A61M 5/14* (2013.01); *A61M 2205/3344* (2013.01); *A61M 2210/0618* (2013.01)

(58) Field of Classification Search
CPC .. A61M 2205/3344; A61M 2210/0681; A61B 2017/00557; A61B 2017/22051; A61B 2090/032; A61B 17/24
See application file for complete search history.

(56) References Cited

U.S. PATENT DOCUMENTS

| | | | |
|---|---|---|---|
| 4,403,988 A | 9/1983 | Binard et al. | |
| 4,439,185 A | 3/1984 | Lundquist | |
| 4,469,484 A | 9/1984 | Kurtz et al. | |
| 4,623,335 A | 11/1986 | Jackson | |
| 4,679,596 A | 7/1987 | Olson | |
| 4,723,938 A * | 2/1988 | Goodin | A61M 25/10182 604/920 |
| 5,085,249 A * | 2/1992 | Dragan | A61M 25/104 604/920 |
| 5,213,115 A | 5/1993 | Zytokovicz et al. | |
| 5,449,344 A | 9/1995 | Taylor et al. | |
| 5,556,386 A | 9/1996 | Todd | |
| 6,110,144 A | 8/2000 | Choh et al. | |
| 9,238,125 B2 | 1/2016 | Vaccaro et al. | |
| 9,474,877 B2 | 10/2016 | Mooney et al. | |
| 9,770,577 B2 | 9/2017 | Li et al. | |
| 10,130,799 B2 | 11/2018 | Kesten et al. | |
| 10,737,077 B2 | 8/2020 | Li et al. | |
| 2006/0009779 A1 | 1/2006 | Collins et al. | |
| 2010/0179488 A1 | 7/2010 | Spiegel et al. | |
| 2010/0211007 A1 | 8/2010 | Lesch, Jr. et al. | |
| 2011/0054395 A1 | 3/2011 | O'Dea et al. | |
| 2011/0220116 A1 | 9/2011 | Lowenstein | |
| 2012/0101515 A1 | 4/2012 | Barbod | |
| 2014/0052063 A1 | 2/2014 | Gregory | |
| 2014/0213968 A1 | 7/2014 | Vaccaro et al. | |
| 2016/0058988 A1 | 3/2016 | Kesten et al. | |
| 2016/0310660 A1 | 10/2016 | Burns et al. | |

FOREIGN PATENT DOCUMENTS

| | | |
|---|---|---|
| WO | 9207609 | 5/1992 |
| WO | 9533510 | 12/1995 |

OTHER PUBLICATIONS

International Search Report and Written Opinion, PCT/US2015/049133, dated Dec. 21, 2015, 20 pages.

* cited by examiner

PRESSURE RELIEF FOR A CATHETER BALLOON DEVICE

REFERENCE TO RELATED APPLICATION

This application is a Continuation of U.S. application Ser. No. 15/715,249, filed Sep. 26, 2017, entitled "PRESSURE RELIEF FOR A CATHETER BALLOON DEVICE," which has issued as U.S. Pat. No. 10,737,077, which is a Continuation of U.S. application Ser. No. 14/486,033, filed Sep. 15, 2014, entitled "PRESSURE RELIEF FOR A CATHETER BALLOON DEVICE," which has issued as U.S. Pat. No. 9,770,577, the contents of both of which are incorporated herein by reference.

BACKGROUND

The present disclosure relates to sinus dilation systems and methods. More particularly, relates to inflation devices useful with balloon-based surgical instruments, such as balloon sinus dilation instruments for dilating a portion of a patient's paranasal sinuses in the treatment of sinusitis and other disorders.

The paranasal sinus system is a grouping of four pairs of air-filled cavities that are named for the facial bones in which they are located. The maxillary sinuses surround the nasal cavity, the frontal sinuses are above the eyes, the ethmoid sinuses are between the eyes, and the sphenoid sinuses are within the sphenoid bone at the center of the skull base under the pituitary gland. The paranasal sinuses are lined with respiratory epithelium, are joined to the nasal cavity via small orifices called ostia, and contain secretory tissue that produces a large volume of mucus. This mucus is normally relieved from the sinuses in a specific pattern through the corresponding ostia.

The mucus membrane that lines the paranasal sinuses can become inflamed. This inflammation is known as sinusitis (or rhinosinusitis), and can be caused by various factors such as bacteria, viruses, allergies, anatomical abnormalities, etc. If the mucosa of one of the paranasal sinus passageways becomes inflamed, the passageway can become blocked, trapping mucus. Patients suffering from sinusitis can experience a number of symptoms or complications, such as headache, facial pain, toothache, inner ear problems, etc.

Sinusitis is typically classified as acute (infection lasting 4 or less weeks) or chronic. Many instances of acute sinusitis can be effectively treated with medication (e.g., antibiotics, antihistamines, etc.). Chronic sinusitis may implicate a more invasive treatment option in which the paranasal passageways or affected sinuses are surgically accessed. Conventional sinus surgery entails an incision formed along the side of the nose or through the gums of the upper teeth to provide access to the targeted sinus anatomy. Once accessed, the paranasal sinus passageway in question is surgically enlarged or otherwise altered to facilitate resumption of mucus clearance.

More recently, corrective sinus surgery has been performed endoscopically, minimizing external trauma to the patient. With functional endoscopic sinus surgery (FESS) an endoscope is inserted into the nose. Using visualization through the endoscope, the anatomical and pathological obstructions associated with the sinusitis are removed in order to restore normal mucus clearance. The benefit of FESS (and other intranasal procedures) is the ability to allow for a more targeted approach to the affected sinuses, reducing tissue disruption and minimizing post-operative complications.

An even more recent minimally invasive, intranasal sinus surgery is known as balloon sinus dilation or balloon sinuplasty. Balloon sinus dilation (or simply "sinus dilation") was initially developed to address the post-operative pain and bleeding associated with FESS. In general terms, conventional sinus dilation is an endoscopic, catheter-based procedure for treating sinusitis using a small, flexible balloon catheter to enlarge or dilate the affected sinus passageway(s). When the balloon is correctly located and inflated, it widens the walls of the sinus passageway, with the goal of restoring normal drainage without damaging the sinus lining.

Prior to performing sinus dilation, the inflator is primed to remove air out of the system. An open end of tubing connected to the inflator is placed in a fluid, such as water, and the fluid is drawn into the inflator. The fluid is expelled from the inflator and the process is repeated one or more times. The balloon is then connected to the open end of the tubing and pressurized with the fluid. The system is then ready for use with another fluid, such as saline, for the sinus dilation. Sometimes, due relocation of the balloon or other reasons, the system is reprimed. Often there is some residue water still remaining in the balloon from the prior priming. This results in additional fluid in the system than potentially realized or desired. The additional fluid in the system can result in overfilling, or over pressurizing, the balloon during sinus dilation.

When performing sinus dilation, the surgeon inserts a sinus guide catheter or cannula through the nostril (or naris) to gain access to the affected sinus ostia (opening) under endoscopic visualization. A guide wire and/or illumination system are then introduced into the targeted sinus via the sinus guide catheter. Once access to the intended targeted location is confirmed by light or fluoroscopy, a flexible catheter, carrying a balloon, is introduced into the sinus cavity over the sinus guide wire, locating the balloon in the blocked ostium. In this regard, the illumination system provides transcutaneous (through the skin) light transmission that the surgeon relies upon when estimating desired balloon placement. Once the desired balloon position has been visually confirmed, the balloon is gradually inflated to dilate the narrowed or blocked ostium. The balloon is then deflated and removed. Next, an irrigation catheter may be advanced over the guide wire to flush out mucus. Finally, the sinus irrigation catheter is removed from the sinus to allow the sinus cavity to drain any mucus. The procedure may be repeated on the other side of the sinus or in a different sinus area (e.g., frontal, sphenoid, or maxillary). Re-priming of the system may be performed prior to beginning the procedure in the next sinus area.

While highly promising, existing sinus dilation systems and methods have several drawbacks. As highlighted by the above, available sinus dilation systems require multiple steps and multiple instruments. While the guide wire can facilitate accessing the targeted sinus site and use of a flexible balloon catheter, surgeons must be trained in the correct use of the guide wire, and the guide wire represents an added cost. Further, the required illumination source and use thereof is time-consuming and relatively expensive. Moreover, a surgeon is required to estimate a location of the targeted ostium only by illumination through the patient's skin. In some instances, the guide wire and/or illumination source may inadvertently be located in a "blind hole". As a point of reference, regions of the sinus system are pneumatized by various cells in most patients. These cells can build over time, collectively creating an anatomic variation. In some instances, for example, Type II cells can occur at the frontal sinus and can progress to a level that is grossly akin to the frontal sinus ostium. It is estimated that as many as 25% of patients suffering from sinusitis of the frontal sinus have Type II cells. When internally illuminated (and viewed externally), a region of the Type II cell cluster may appear (or "feel") quite similar to the natural frontal sinus ostium, leading the surgeon to incorrectly assume that the desired ostium has been accessed. When the balloon is subsequently inflated, it may actually occlude the ostium rather than open the ostium.

In addition to the above concerns, the inflation devices utilized with available sinus dilation systems have several drawbacks. As a point of reference, balloon catheters have long been employed for various surgical procedures (e.g., angioplasty, intravascular stent deployment, kyphoplasty, etc.), and inflation devices well-suited for these applications are widely available. Although the anatomical constraints and performance requirements associated with balloon sinus dilation are quite different from other balloon catheter procedures, existing balloon sinus dilation systems default to the already-available inflation devices. Available inflation devices are typically quite large (in order to maintain a sufficient volume of inflation fluid), full featured (e.g., include one or more gauges that display pressure(s) within the device), and complicated to use. For example, mechanical pressure gauges (with dial-type display), electronic pressure gauges (with digital-type display), are included with available balloon catheter inflation devices. While necessary for many balloon catheter procedures, a constant display of current system pressure is of less importance with balloon sinus dilation. These gauges render existing inflation devices highly expensive, especially where the inflation device is intended to be disposable. Further, the gauge(s) may need to be calibrated prior to each use, thereby increasing the time required to complete the procedure. Conversely, other, less-complex inflation devices (e.g., a simple syringe) provide no indication of system pressure, and are void of any warnings or pressure relief when system pressure exceeds particular level(s).

In light of the above, a need exists for improved inflation devices useful with sinus dilation systems and other balloon-based surgical procedures.

SUMMARY

One aspect provides an inflation device for selectively inflating a balloon of a surgical instrument including a syringe, a connector, a mechanical pressure indicator, and a relief port. The syringe includes a plunger slidably disposed within a barrel. The connector fluidly connects an outlet of the syringe with a surgical instrument balloon to establish a closed inflation system between the syringe and an interior of the balloon. The mechanical pressure indicator is associated with the syringe and configured to transition from a non-alert state to an alert state when a pressure of the inflation system has reached a predetermined level. The relief port is associated with the mechanical pressure indicator and configured to relieve a pressure of the inflation system when the system reaches or exceeds the predetermined level.

Another aspect provides an inflation device for selectively inflating a balloon of a surgical instrument including a syringe, a connector, a mechanical pressure indicator, and a relief port. The syringe includes a plunger slidably disposed within a barrel. The connector fluidly connects an outlet of the syringe with a surgical instrument balloon to establish a closed inflation system between the syringe and an interior of the balloon. The mechanical pressure indicator is associated with the syringe and configured to indicate when the inflation system pressure has reached a first predetermined level. The relief port is configured to maintain the inflation system pressure below a second predetermined level, wherein the second predetermined level is higher than the first predetermined level.

Another aspect provides an inflation system for dilating a region of a patient's nasal sinus passageways including a sinus dilation instrument and an inflation device. The sinus dilation instrument includes a probe configured to deliver a balloon to a paranasal sinus target site. The inflation device is used for inflating the balloon. The inflation device includes a syringe assembly, a mechanical pressure indicator, a connector, and a relief port. The syringe assembly is operable to deliver fluid through an outlet. The mechanical pressure indicator is associated with the syringe assembly and configured to transition from a non-alert state to an alert state when a pressure of the inflation system has reached a predetermined level. The connector fluidly connects the outlet with the sinus dilation instrument to establish a closed inflation system between the syringe assembly and an interior of the balloon. The relief port is associated with the mechanical pressure indicator and configured to relieve a pressure of the inflation system when the system exceeds the predetermined level.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Figure 1:
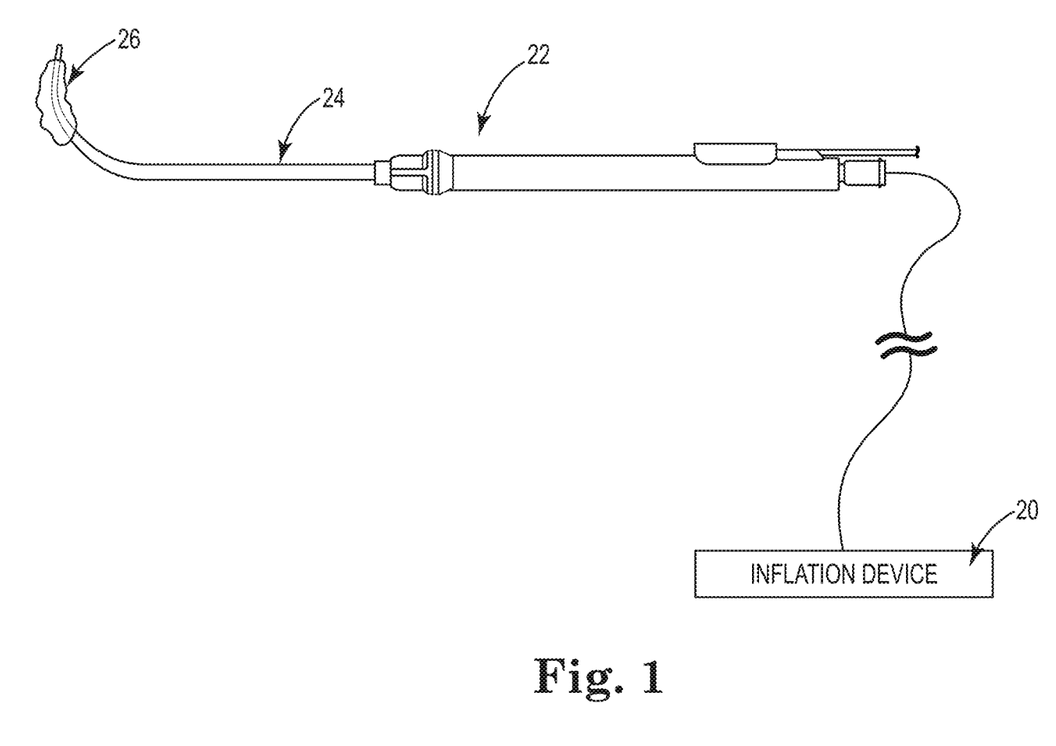
FIG. 1 is a schematic illustration of a surgical system including an inflation device and a balloon sinus dilation instrument.

Aspects of the present disclosure relate to inflation devices useful with balloon-based (or balloon-carrying) surgical instruments, for example, with sinuplasty and other balloon-based paranasal sinus procedures. The inflation devices of the present disclosure can be provided as a stand-alone device, or can be included as part of a surgical system some examples of which are described in U.S. application Ser. No. 13/725,716 entitled "Sinus Dilation System and Method" filed Dec. 21, 2012 and the disclosure of which is incorporated herein by reference in its entirety. In general terms, and as shown in FIG. 1, inflation devices 20 of the present disclosure can be used with a sinus dilation instrument 22. The sinus dilation instrument 22 can assume a wide variety of forms, and more generally includes a probe (e.g., a rod or tube) 24 carrying a balloon 26. The probe 24 is sized and shaped to deliver the balloon 26 to a paranasal sinus target site (e.g., a sinus ostium) via a patient's nostril or naris or other conventional approach such as canine fossa or open approach. Once positioned, the inflation device 20 is operated to inflate the balloon 26, with the so-inflated balloon dilating the target site. As described below, the inflation devices 20 of the present disclosure do not include any pressure gauges (mechanical or electrical) and do not display pressure readings. However, the inflation devices 20 will alert a user when a desired inflation pressure is reached. Thus, the simplified inflation devices 20 of the present disclosure are, as compared to conventional surgical balloon catheter inflation devices, highly cost effective and intuitive/easy to use.

Figure 2A:
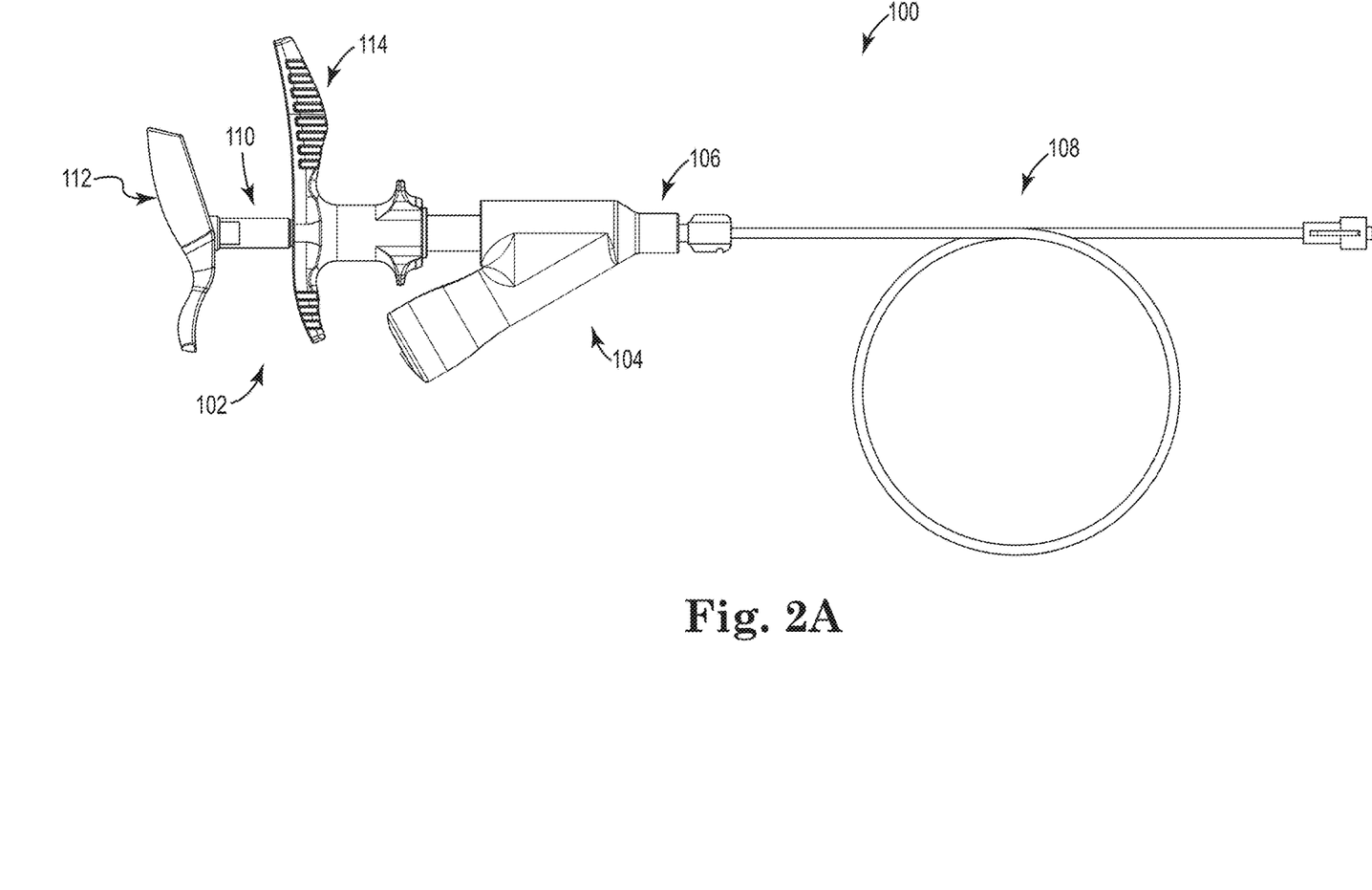
FIG. 2A is a side view of an inflation device in accordance with principles of the present disclosure and in a non-alert state.
Figure 2B:
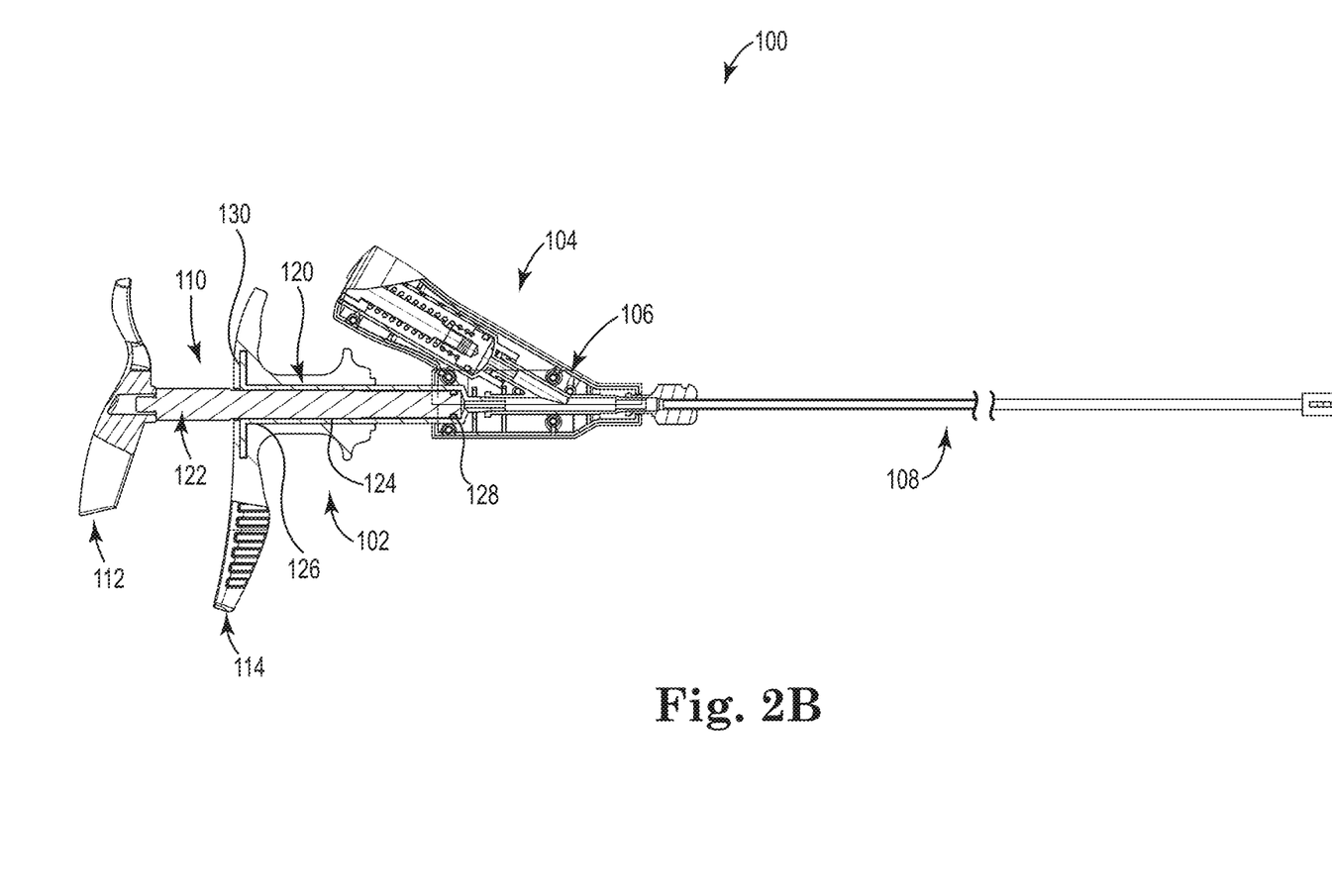
FIG. 2B is a cross-sectional view of the inflation device of FIG. 2A.

With the above in mind, one embodiment of an inflation device 100 in accordance with principles of the present disclosure and useful with sinus dilation instruments is shown in FIGS. 2A and 2B. The inflation device 100 includes a syringe assembly 102, a mechanical pressure indicator 104, a connector assembly 106, and optional tubing 108. Details on the various components are provided below. In general terms, the syringe assembly 102 is manually operable to deliver pressurized fluid (e.g., for inflating the sinus dilation instrument balloons of the present disclosure). The mechanical pressure indicator 104 is fluidly connected to an outlet of the syringe assembly 102 via the connector assembly 106 and provides a visual indication (e.g., transitions from a normal or non-alert state of FIG. 2B (also shown in FIG. 3A) to an alert state (shown in FIG. 3B)) when a pressure of fluid at the syringe assembly 102 reaches a first pre-determined level, and limits the inflation system pressure to a second pre-determined level higher than the first pre-determined level that transitions the mechanical pressure indicator 104 to the alert state (shown in FIG. 3C). The tubing 108, where provided, can be of a conventional form for fluidly connecting an outlet of the connector assembly 106 with the sinus dilation instrument 22 (or other instrument of interest).

Figure 3A:
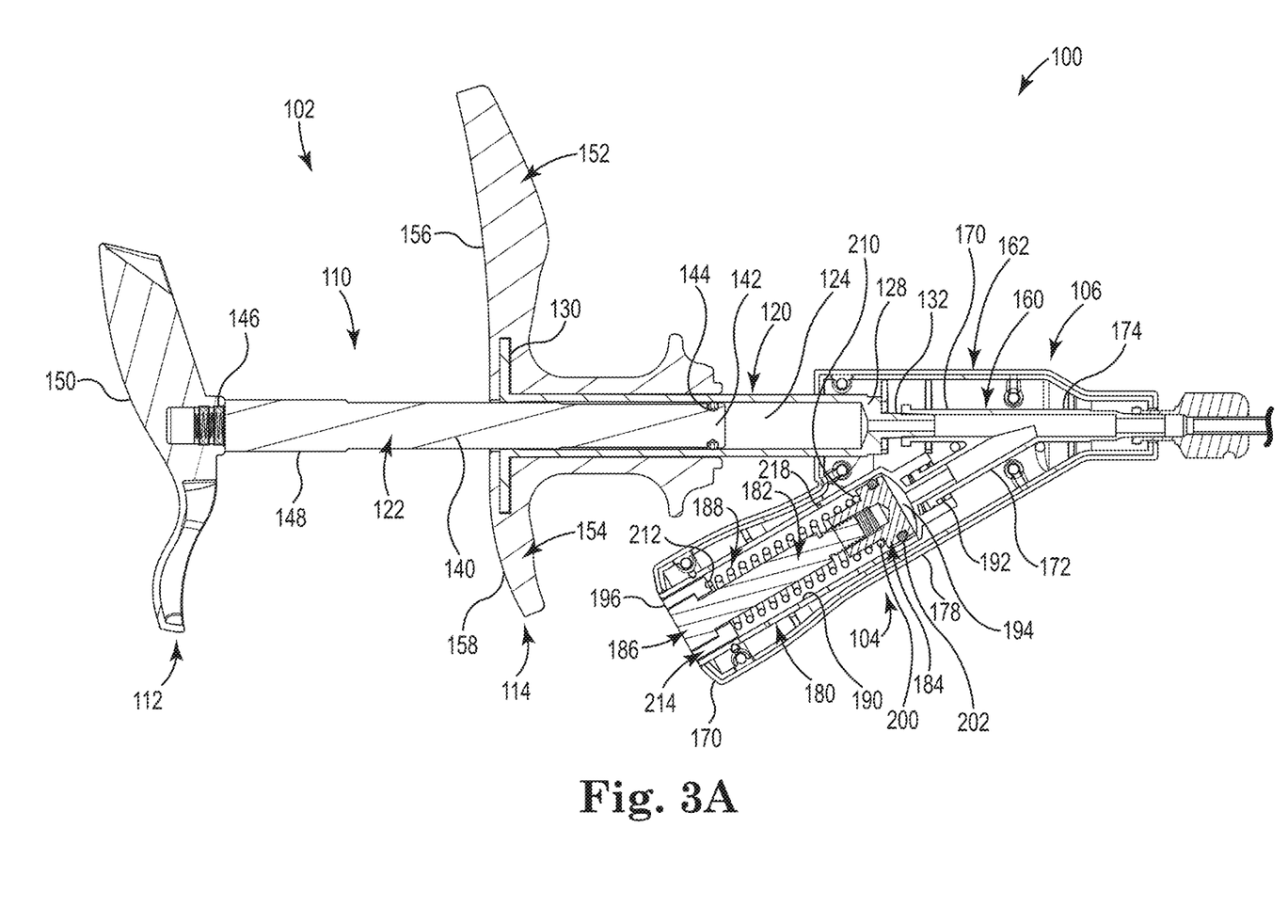
FIG. 3A is an enlarged cross-sectional side view of a portion of the inflation device of FIG. 2A in a non-alert state.

The syringe assembly 102 includes a syringe 110, an optional push handle 112 and an optional grip handle 114. The syringe 110 can be of a conventional design, and includes a barrel 120 and a plunger 122. The barrel 120 defines a chamber 124 extending between a proximal end 126 and a distal end 128. A flange 130 is optionally formed at the proximal end 126. Regardless, and as best shown in FIG. 3A, the chamber 124 is sized to maintain a volume of fluid appropriate for inflating the sinus dilation instrument balloon 26 (FIG. 1). The fluid can be dispensed from the chamber 124 via the distal end 128. The barrel 120 can form an outlet port 132 extending from the distal end 128. The outlet port 132 is open to the chamber distal end 128 and provides a smaller inner diameter (thus serving as a stop to forward movement of the plunger 122).

The plunger 122 includes a shaft 140 carrying or forming a head 142. The shaft 140 is slidably arranged with the chamber 124, including the head 142 forming a sealed relationship with the barrel 120. Thus, the head 142 can be or can carry an O-ring 144 or rubber membrane. The plunger 122 terminates at an end 146 opposite the head 142. A trailing region 148 adjacent the end 146 can have an outer diameter greater than a diameter of a remainder of the plunger 122, with this increased size serving as a stop to attempted over insertion of the plunger 122 within the barrel 120. The trailing region 148 has a diameter greater than the diameter of the chamber distal end 128 and/or the grip handle 114 (as described below) to physically prevent the plunger 122 from being overtly pressed relative to the barrel 120.

In some embodiments, the syringe 110 is a 3 mL syringe, and is configured to limit travel of the plunger 122 such that a volume of approximately 1.9 mL of inflation medium can be maintained within the chamber 124. Other sizes and volumes are also acceptable.

The handles 112, 114, where provided, promote convenient grasping and handling of the inflation device 100 by a user, as well as operation of the syringe 110. The push handle 112 is configured to be mounted to the plunger end 146 and defines or forms a contoured face 150 configured to ergonomically receive the palm and/or thumb of user's hand otherwise acting to apply a pressing force onto the push handle 112 (and thus the plunger 122). In other embodiments, the push handle 112 can assume a variety of other shapes, and can be integrally formed by the plunger 122.

The grip handle 114 is configured for assembly or molding over the barrel 120, for example forming a slot that accommodates the flange 130. The grip handle 114 defines opposing finger projections 152, 154 each forming a grasping face 156, 158 sized and shaped to ergonomically receive one or more fingers of a user's hand otherwise acting to apply a pressing force onto the push handle 112. With this optional construction, then, a user's palm is placed against the push handle face 150 while the user's finger are placed against the grip handle grasping faces 156, 158; the user's hand is then squeezed to apply a pushing force onto the push handle 112/plunger 122.

The connector assembly 106 includes a connector 160 and a cover 162. The connector 160 can assume a variety of forms and in some embodiments is a Y-connector defining first and second inlet tubes 170, 172, and an exit tube 174. The exit tube 174 is fluidly connected to the inlet tubes 170, 172, and is configured for connection to the auxiliary tubing 108. While the connector 160 has been described as being a component discrete from the syringe assembly 102 and the pressure indicator 104, in other embodiments, the connector 160 is integrally formed by or with the syringe 110 and/or the pressure indicator 104.

The cover 162 is an optional component configured to more robustly stabilize the connector 160 relative to the syringe assembly 102 and the pressure indicator 104. As generally reflected in FIG. 2B, the cover 162 forms various internal features (e.g., ribs) to which the barrel 120, the connector 160, and a component of the pressure indicator 104 are mounted. For reasons made clear below, a side 176 of an indicator region 178 of the cover 162 forms an opening 180. In other embodiments, the cover 162 can be omitted.

The mechanical pressure indicator 104 is shown in greater detail in FIGS. 3A-3C and 4A-4D, and includes a housing 180, a rod 182, a head 184, an indicator body 186, and a spring or other biasing device 188. In general terms, the rod 182 is slidably disposed within the housing 180, and maintains the head 184 and the indicator body 186. The spring 188 biases the rod 182 to the normal or non-alert state reflected in FIG. 3A. The mechanical pressure indicator 104 transitions to the alert state of FIG. 3B when a pressure acting upon the head 184 (in a direction opposite a bias of the spring 188) overcomes a force of the spring 188. The mechanical pressure indicator 104 further transitions to an alert pressure relief state of FIG. 3C when the pressure acting upon the head 184 further overcomes the force of the spring 188 transitioning the head 184 further away from the port 192.

The housing 180 is a tubular body defining a primary chamber 190 and a port 192. A common passageway 194 extends through the chamber 190 and the port 192, and is open at a trailing end 196 of the housing 180. Further, a diameter of the passageway 194 is reduced at the port 192.

The head 184 and the indicator body 186 are connected to the rod 182 at opposite ends thereof. The head 184 includes or carries a sealing membrane 200 (along with an optional O-ring 202) having a diameter approximating a diameter of the passageway 194 within the chamber 190, and is configured to establish a fluid-tight seal against an inner wall of the housing 180 as shown. The fluid tight seal of the sealing membrane 200 (and optionally o-ring 202) of the head 184 within the housing effectively separates the chamber 190 into a first portion that is in fluid communication with the syringe assembly 102 and a second portion that is fluidly separated from the syringe assembly 102. Notably, the first and second portions of the chamber 190 correspondingly change in volume and size as the head 184 slidably moves within the chamber (i.e., as the volume of the first portion increases the volume of the second portion decreases). A diameter of the rod 182 is less than a diameter of the head 184. The indicator body 186 can have a diameter greater than that of the rod 182, and is sufficiently sized to be completely received within the chamber 190. The indicator body 186 can assume various forms (e.g., plastic) and in some embodiments is brightly colored (e.g., red). The indicator body 186 is, in some embodiments, integrally formed with the rod 182.

Figure 3B:
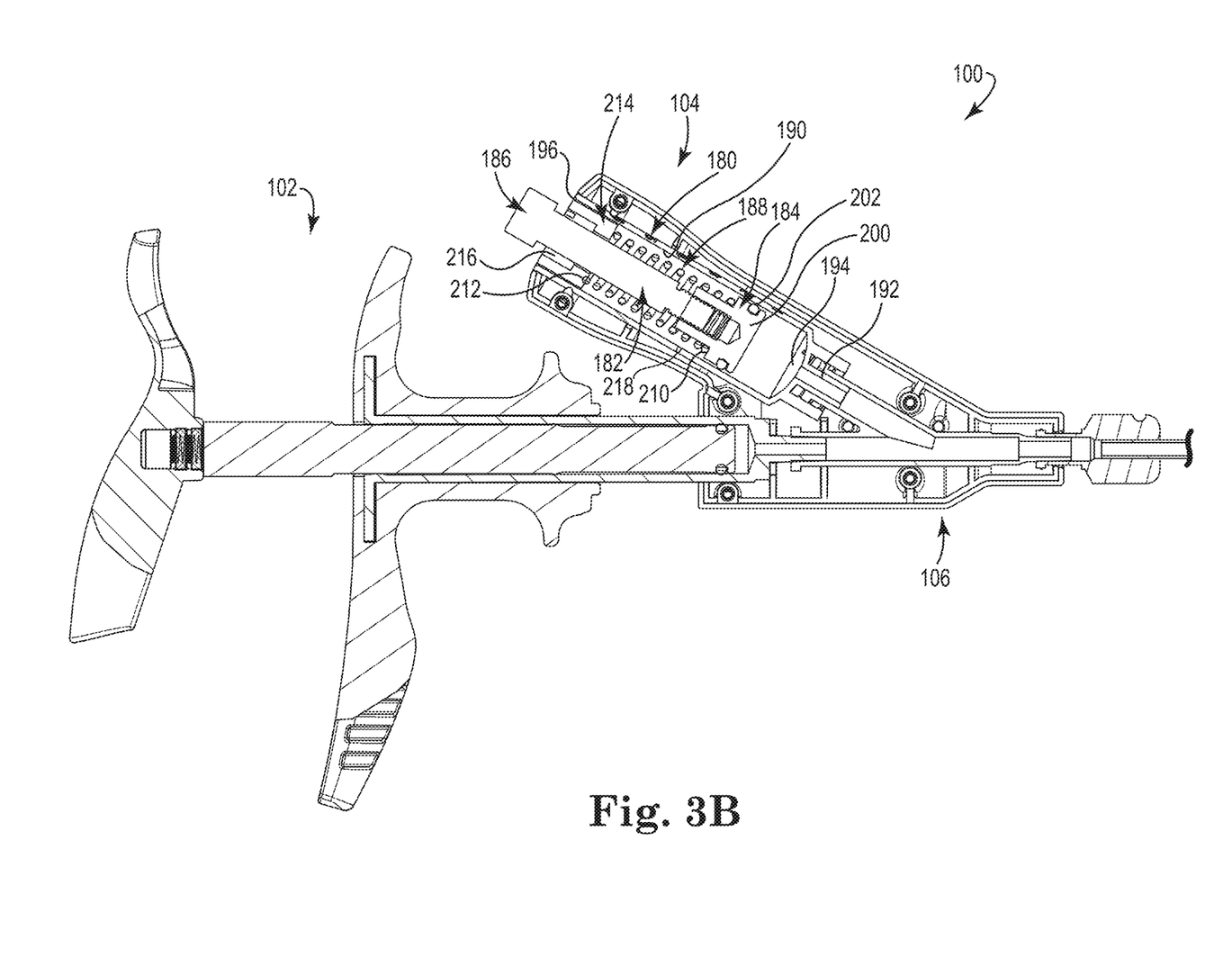
FIG. 3B is a cross-sectional side view of the portion of the inflation device, of FIG. 3A in an alert state.

The spring 188 is selected to have a known spring force constant as described below. The spring 188 is slidably disposed about the rod 182, and is attached at a first end 210 to the head 184. An opposing, second end 212 of the spring 188 is robustly mounted within the chamber 190. For example, the mechanical pressure indicator 104 can include an end cap 214 mounted within the passageway 194 adjacent the trailing end 196 and providing a reduced diameter surface against which the second end 212 of the spring 188 is maintained. As best shown in FIG. 3B, the end cap 214 forms an internal bore 216 within which the indicator body 186 is slidably received. For reasons made clear below, with constructions in which the housing 180 is transparent or nearly transparent, the end cap 214 can be opaque or otherwise configured to visually obscure the indicator body 186 when located within the end cap 214.

Upon final assembly, the spring 188 biases the head 184 toward the port 192, with the head 184 and/or the sealing member 200 establishing a fluid seal with the chamber 190. A length of the rod 182, the head 184 and the indicator body 186 is such that in the normal, non-alert state or condition of FIG. 3A, the indicator body 186 is located entirely within the housing 180, and is thus exteriorly hidden from view (e.g., one or both of the housing 180 and the end cap 214 are opaque thus obscuring the indicator body 186). Conversely, when the head 184 is forced rearward within the chamber 190 as described below, at least a portion of the indicator body 186 is located exterior the housing 180 (and the cover 162) in the alert state of FIG. 3B and the alert pressure relief state of FIG. 3C, and thus is visible to a user from an exterior of the housing 180.

Construction of the inflation device 100 includes assembling the connector first inlet tube 170 to the syringe outlet port 132, and the second inlet tube 172 to the pressure indictor port 192. Thus, the connector 160 fluidly connects the syringe 110 with the pressure indicator 104, with the outlet tube 174 being fluidly open to the fluid or pressure of (or generated by operation of) the syringe 110. The cover 162, where provided, is assembled to the connector 160, the barrel 120 and the housing 180 as shown. As reflected by FIGS. 2A and 2B, during use of the inflation device 100 with the sinus dilation instrument 22 (FIG. 1), the connector outlet tube 174 is fluidly connected to the balloon 26 (FIG. 1), for example via an inflation lumen (not shown) of the sinus dilation instrument and the auxiliary tubing 108. A closed inflation system or path is formed between the inflation device 100 and the balloon 26, and fluid delivered from and/or pressure generated by the inflation device 100 causes the balloon 26 to expand. It will be understood that when dilating a sinus ostium, the structure against which the balloon 26 is placed will resist expansion of the balloon 26, thus creating an elevated pressure within the inflation system. As the user exerts an increased force on the plunger 122 to effectuate desired balloon inflation (e.g., transitions from the arrangement of FIG. 3A to the arrangement of FIG. 3B), the inflation system pressure will further increase. It may be desirable to alert a user when the inflation system pressure has reached a certain level. With this in mind, the mechanical pressure indicator 104 is fluidly exposed to the inflation system pressure, with the pressure exerting a force on the head 184 in a direction opposite a biasing force of the spring 188. At inflation system pressures below the spring force constant of the spring 188, the force generated by the spring 188 exceeds the force applied on the head 184 by the inflation system pressure, and the pressure indicator 104 remains in the non-alert state of FIGS. 2A and 2B (i.e., the indicator body 186 remains hidden within the housing 180 and/or end cap 214). When the inflation system pressure exceeds the force applied by the spring 188, the head 184, and thus the rod 182 and the indicator body 186, are displaced in a rearward direction to the alert state of FIG. 3B. The displacement locates the indicator body 186 outside of the housing 180 where it is easily seen or visually perceived by a user. Even though the indicator body 186 is visible to alert a user of having effectuated the desired balloon inflation and inflation system pressure, in some cases, the user may be continue to exert additional increased force on the plunger 122. Through the continued increased force on the plunger 122, the inflation system pressure may continue to increase and exceed the desired level. When the inflation system pressure further increases and exceeds the force applied by the spring 188, the head (and thus the rod 182 and the indicator body 186) are further displaced in the rearward direction than when in the alert state of FIG. 3B and transitions to the alert pressure relief state of FIG. 3C.

Figure 3C:
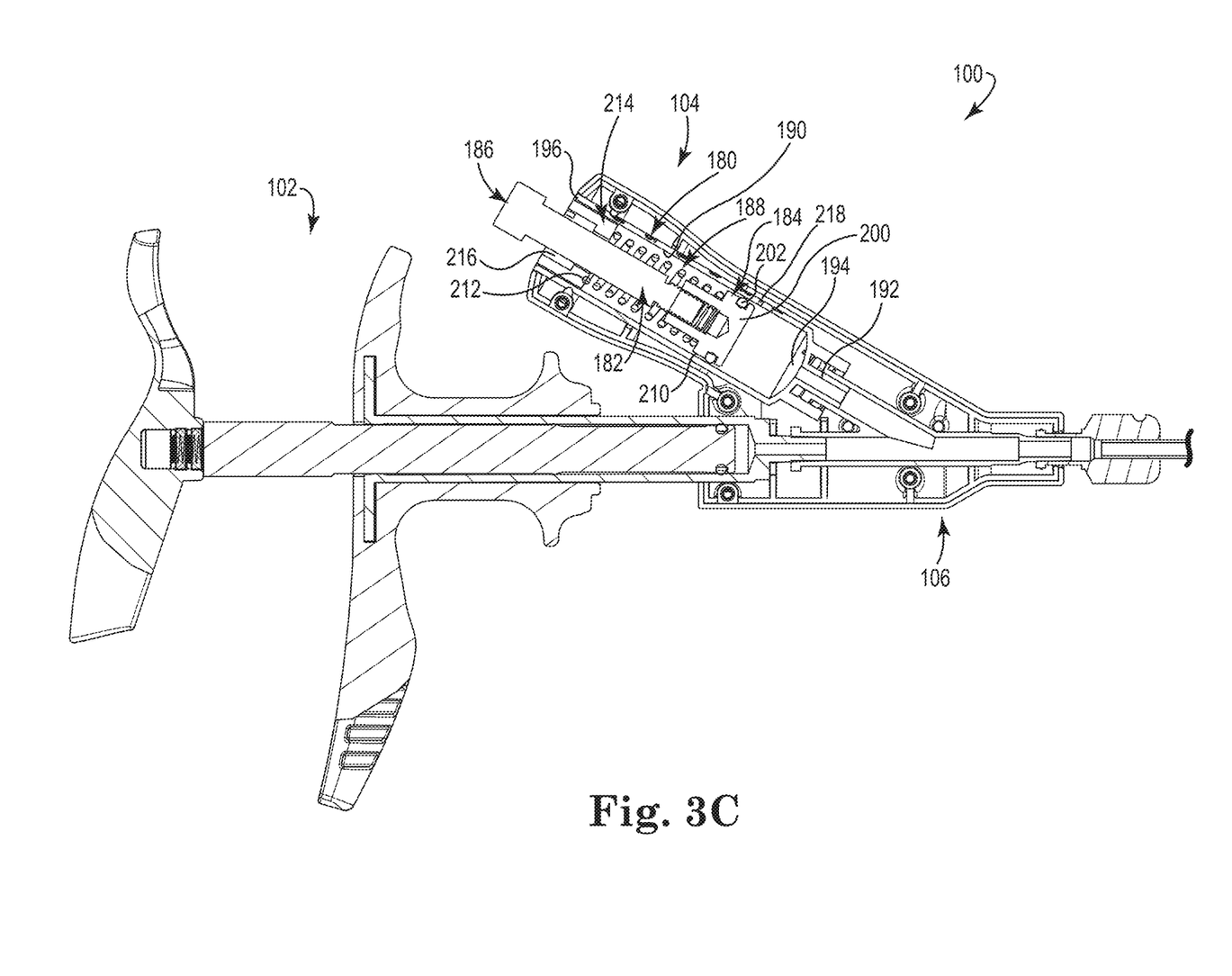
FIG. 3C is a cross-sectional side view of the portion of the inflation device, of FIG. 3A in a pressure relief state.

With the above explanations in mind, and with specific reference to FIGS. 3A through 3C, a spring force constant can be selected for the spring 188 that corresponds with a desired, target inflation system pressure. Stated otherwise, based upon one or more factors such as expected sinus dilation anatomical constraints, system component limitations (e.g., burst strength of the sinus dilation balloon 26 (FIG. 1)), etc., a target inflation system pressure can be determined and the spring 188 is selected or constructed to exhibit a spring force constant that is approximately equal to the force associated with the determined target inflation system pressure. In related embodiments, the spring force constant of the spring 188 in combination with a preload force established upon the spring 188 upon assembly within the housing 180 is selected such that the indicator 104 transitions to the alert state at the predetermined inflation system pressure target limit. In one embodiment, the spring 188 is preloaded to 29.3+/−0.5 pounds. Regardless, during use, once the indicator body 186 becomes visible (e.g., the alert state of FIG. 3B), the user can readily understand that the desired target inflation system pressure has been reached and that no additional force should be applied to the plunger 122. In some embodiments, an interface between the indicator body 186 and the end cap 214 (or other component of the indicator 104) is such that a tactile and/or audible "click" is generated as the indicator body 186 displaces from the end cap 214. For example, a slight frictional interface can be established with movement of the indicator body 186 producing a tactile and/or audible "click" (or other noise) that can be felt and/or heard by a user otherwise handling the inflation device 100. The optional tactile attribute in transitioning from the non-alert state to the alert state can be beneficial in low light environments.

By way of example, a balloon pressure of approximately 2 ATM is typically required to break paranasal bone and other tissue as part of a sinus ostium dilation procedure. Successful sinus dilation normally does not require a balloon pressure greater than 10 ATM, and sinus dilation procedures conventionally specify an upper limit of 13 ATM. Balloon pressures (or attempted balloon pressures) above 13 ATM are unnecessary and may lead to patient complications, instrument failure, or both. In some embodiments, then, the inflation device 100 (as well as other embodiment inflation devices described below) is configured to transition to the alert state when the inflation system pressure reaches about 10 ATM and an alert pressure relief state when the pressure exceeds 10 ATM. In other words, in some embodiments, the inflation device 100 can immediately transition from the alert state to the alert pressure relief state upon exceeding a first predetermined desired inflation system pressure. In other embodiment, the inflation device 100 is configured to transition to the alert state when the inflation system pressure reaches the first predetermined inflation system pressure and does not transition to the alert pressure relief state until a second predetermined inflation system pressure (greater than the first predetermined inflation system pressure) is reached.

In some embodiments, a volume of the mechanical pressure indicator 104 is significantly larger than that of the syringe 110. Stated otherwise, the volume of the indicator chamber 190 (FIG. 3B) is greater than a volume of the syringe chamber 124. With this construction, when the desired inflation system pressure is reached, displacement of the head 184 effectively absorbs the additional fluid displaced by the syringe plunger 122, and limits the amount of additional pressure that can be produced, thus reducing the risk of an accidental over-pressure condition. In related embodiments, a stroke length of the syringe 110 (i.e., longitudinal length of the plunger 122 from the head 142 to the trailing region 148) can be selected so as to not exceed an expected distance of travel otherwise needed for most sinus dilation inflation procedures. In other, related embodiments, the indicator body 186 (or any other structure specifically included to provide a visual "warning" to a user) can be omitted, with the pressure indicator 104 beneficially providing the pressure accumulation/limits in accordance with principles of the present disclosure.

Due to factors such as excess fluid in the system resulting from residue fluid remaining in the system from repriming, for example, over-pressuring of the inflation system can occur. As noted above, an upper limit of 13 ATM is often acceptable, however, pressures exceeding 13 ATM can cause damage. A relief port 218 is included on the housing 180 of the mechanical pressure indicator 104 to prevent the inflation system pressure from exceeding 13 ATM. The relief port 218, when fluidly communicating with the port 192, as discussed more below, provides pressure relief when the inflation system pressure exceeds a predetermined level. In some cases, fluid exits the primary chamber 190 through the relief port 218 when the inflation system pressure is between 10.1 ATM and 13 ATM.

With embodiments in which the inflation device 100 is used in performing a sinus dilation procedure, methods in accordance with principles of the present disclosure include selecting a sinus dilation instrument (e.g., the sinus dilation instrument 22 of FIG. 1) appropriate for accessing the paranasal target site. The tubing 108 is fluidly connected to the instrument's balloon 26 (FIG. 1) and the connector assembly 106 (as shown, for example, in FIG. 2B). The syringe 110 can be pre-loaded with the inflation medium, or the user can fill the syringe 110 with a desired volume of the inflation medium prior to connection with the tubing 108. Regardless, the balloon 26 is initially deflated, the syringe assembly 102 is in the loaded state of FIG. 3A, and the pressure indicator 104 is in the non-alert state of FIG. 3A. The sinus dilation instrument 22 is manipulated by a user to locate the balloon 26 at the target site, for example by directing the probe 24 through the patient's nostril and along the desired paranasal passageways. Once the balloon 26 has been located at the paranasal target site, the inflation device 100 is operated to expand the balloon 26. In other embodiments, the tubing 108 is fluidly connected to the balloon 26 after first directing the balloon to the paranasal target site.

Expansion or inflation of the balloon 26 occurs as the plunger 122 is pressed by the user, forcing the inflation medium into the tubing 108 and increasing pressure within the inflation system. Once the inflation system pressure reaches the predetermined level (e.g., 10 ATM), the pressure indicator 104 self-transitions from the non-alert state of FIG. 3A to the alert state of FIG. 3B. The indicator body 186 becomes readily visible to the user, alerting the user that the target inflation system pressure has been reached. A tactile and/or audible alert is also generated. Knowledge that the target inflation system pressure has been reached confirms for the user that a desired re-shaping of the paranasal target site has occurred (e.g., necessary breakage of nasal bone and other tissue). The user can then deflate the balloon 26 by operating the syringe 110 in the opposite direction, and end the procedure. Alternatively, the user may decide to further increase the inflation system pressure by applying additional force on to the plunger 122. The inflation device 100 will permit the inflation system pressure to increase beyond the target pressure (i.e., after transitioning to the alert state, the inflation system pressure can be further increased), but may be limited by a stroke length of the plunger 122 and pressure relief accommodated by the pressure indicator 104 (e.g., 12 ATM).

Figure 4A:
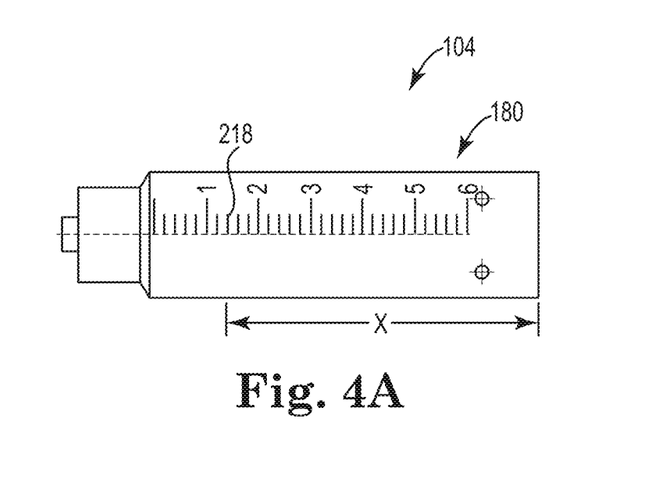
FIG. 4A is an enlarged side view of the mechanical pressure indicator of inflation device of FIG. 3A in the non-alert state.
Figure 4B:
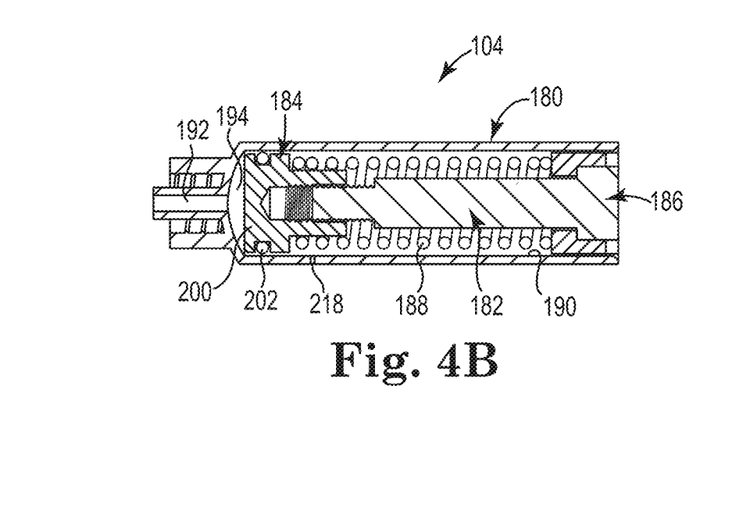
FIG. 4B is an enlarged cross-sectional side view of the mechanical pressure indicator of inflation device of FIGS. 3A and 4A in a non-alert state.
Figure 4C:
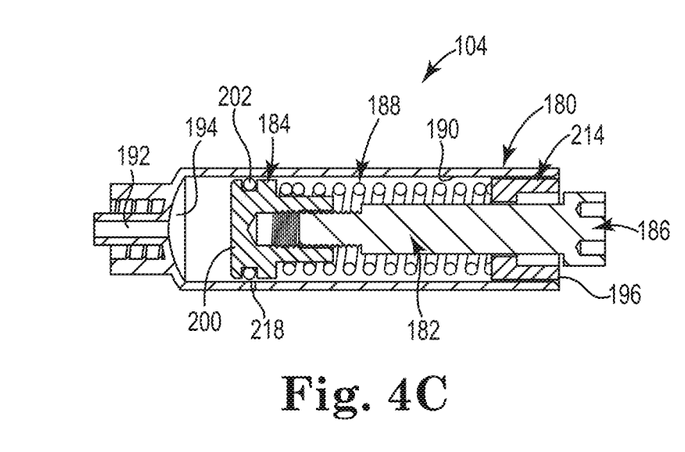
FIG. 4C is an enlarged cross-sectional side view of the mechanical pressure indicator of inflation device of FIG. 3B in an alert state.
Figure 4D:
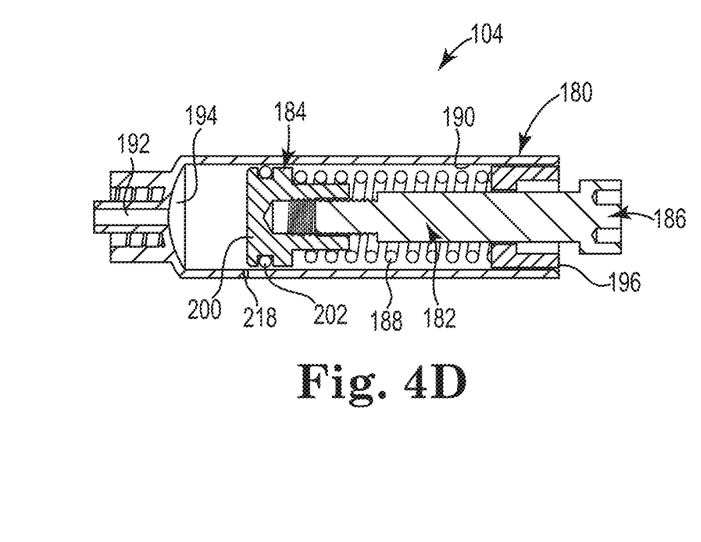
FIG. 4D is an enlarged cross-sectional side view of the mechanical pressure indicator of inflation device of FIG. 3C in the pressure relief state.

With additional reference to FIGS. 4A-4D, after the pressure indicator 104 self-transitions from the non-alert state of FIGS. 3A and 4B to the alert state of FIGS. 3B and 4C, further increases in the inflation system pressure beyond the predetermined level (e.g., 10 ATM) of the alert state or a higher, second predetermined level (e.g., 11 ATM), self-transitions the mechanical pressure indicator from the alert state of FIGS. 3B and 4C to the over-pressure state of FIGS. 3C and 4D. As noted above, the syringe 110 can be pre-loaded with the inflation medium, or the user can fill the syringe 110 with a desired volume of the inflation medium prior to connection with the tubing 108. Prior to the inflation medium, the system is primed, and in some cases reprimed, sometimes causing excess fluid in the system above the pre-loaded or desired volume of the inflation medium. This excess fluid in the system can cause inflation system pressures in excess of the predetermined level. In the non-alert state of FIG. 3A and the alert state of FIG. 3B, the sealing member 200 and o-ring 202 of head 184 blocks and prevents fluid from passing through the relief port 218, but under conditions of over-pressure, the head 184 will transition toward the trailing end of the housing 180 to expose the relief port 218 through which fluid will flow and exit the closed system. As the inflation system pressure is raised above the predetermined level, pressure against the head 184 and biasing mechanism 188 increases and the head 184 slidably transitions to a position that fluidly exposes the relief port 218 to the fluid in the passageway 194 of primary chamber 190. The mechanical pressure indicator 104 transitions to the pressure relief state of FIG. 3C when a pressure acting upon the head 184 (in a direction opposite a bias of the spring 188) overcomes a force of the spring 188 and exposes the relief port 218 to the fluid within the first portion of the primary chamber 190. Excessive inflation system pressure may be alleviated by fluid exiting the closed system of the inflation device 100 via the relief port 218. Excess fluid is exits the housing 180 through relief port 218 and can be expelled to within cover 162, where provided, or simply be expelled exterior the entire inflation device 100. The spring 188 is sufficiently preloaded to bias/return the head 184 to a position that fluidly closes the relief port 218 from the first portion of the chamber 190 and the closed inflation system when the pressure returns to the predetermined level transitioning from the alert pressure relief state of FIGS. 3B and 4C to the alert state of FIGS. 3B and 4C. The resealing of the relief port 218 prevents further pressure relief and maintains the inflation system pressure at the predetermined level.

The relief port 218 is positioned along the length of the housing 180 such that the relief port 218 remains above the o-ring 202 (or other sealing member) of the head 184 and the inflation device 100 pressurizes the balloon 26 (FIG. 1) to the predetermined level and the indicator body 186 functions to alert a user of achieving the predetermined level. The relief port 218 is further positioned such that the o-ring of the head 184 (or other sealing member) can transition above the relief port 218 to fluidly expose the relief port 218 and relieve inflation system pressure of the balloon 26. The relief port 218 extends fully through side walls of the housing 180 permitting fluid to exit the housing 180 and is fluidly open between the interior and exterior of the housing 180. In one embodiment, the relief port 218 is 0.016 inches in diameter. The relief port 218 can be drilled or otherwise suitably formed in the side wall of the housing 180. As illustrated in FIG. 4A, the relief port is positioned a distance "x" from the trailing end 196 of the housing 180. In one embodiment, a single relief port 218 is included on the side wall of the housing 180 positioned at the distance "x" of 1.522 inches, as described in more detail below.

In one example embodiment, the primary chamber is 1.84 inches long and the relief port is positioned 1.522 inches from the trailing end 196 of the housing 180. A spring assembly including the biasing device 188 and head 184 is between 1.60 and 1.81 inches in length when unbiased. The sealing member 200 is 0.50 inches in length and the o-ring 202 is positioned 0.05 inches from the terminal end of the head 184 adjacent to the port 192.

EXAMPLE

Figure 5A:
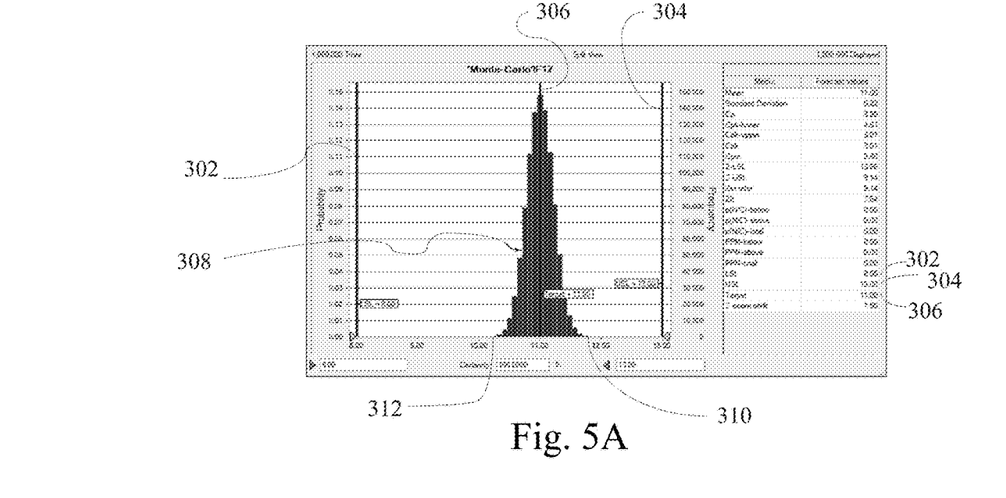
FIGS. 5A-5B are diagrammatic illustrations of a simulation of an example inflation device.
Figure 5B:
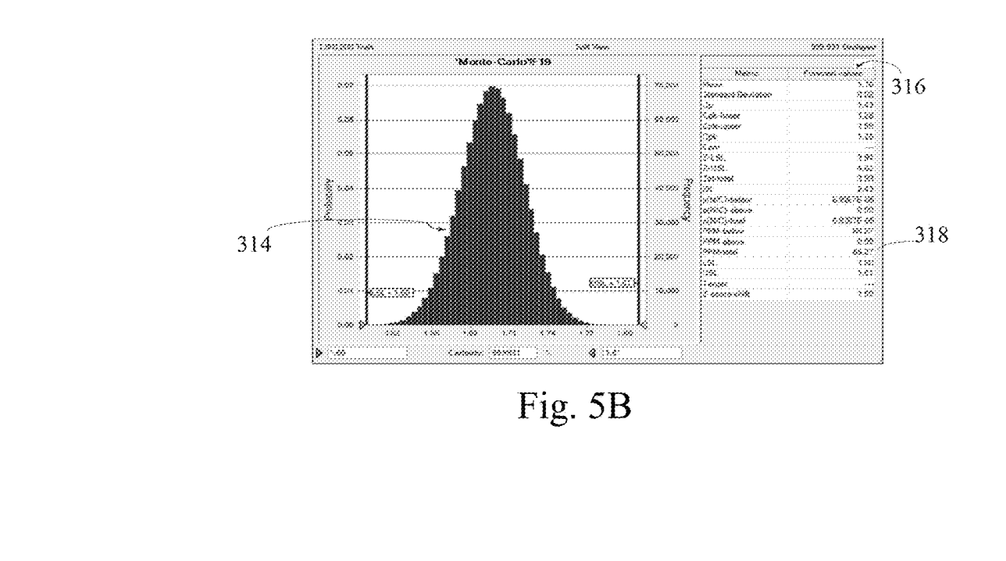

A Monte Carlo analyses and optimizations were performed with regard to the relief port. In the following example simulation, as illustrated in FIGS. 5A and 5B, vented pressures of 100,000 mechanical pressure indicators were analyzed with a lower specified limit set 302 at 8.00 ATM and an upper specified limit 304 set at 13.00 ATM. As described above, pressures above 13.00 ATM can cause undesirable damage to the sinus cavity or balloon and pressure below 8.00 ATM can cause fluid leaks. A target pressure 306 was established at 11.0 ATM. The relief port was simulated to be 1.522 inches from trailing end of the mechanical pressure indicator housing. The spring assembly length (from the terminal face of the head to the second end of the spring) was established between 1.600 and 1.810 inches in an unbiased state and the chamber length was established at 1.84 inches. A bell curve 308 of the vented pressure is illustrated in FIG. 5A. The maximum venting pressure 310 at the noted relief port position is about 11.8 ATM, well below the 13.00 ATM upper specified limit 304, and the minimum venting pressure 312 at the noted relief port position is about 10.2 ATM, above the 8.00 ATM lower specified limit 302. As shown in FIG. 5A, the mean pressure was 11.00 ATM, equal to the desired target pressure.

It was surprisingly found that a single relief port having a 0.016 inch diameter at 1.522 inches from the terminal end of the housing maintained the desired target pressure 306 without relieving too much pressure such that balloon pressure was decreased below the target pressure. As described above, this provides lower top end of the maximum pressure without making the inflation device non-functional and vent even before the plunger is pressed in the vast majority of units. It was found that positioning the relief port location approximately 1.5 inches from the terminal end provides the minimum indication larger for easy viewing.

FIG. 5B illustrates the number of indicators that would likely fail with the relief port at 1.522 inches from the terminal end of the housing. By failing, it is meant that the relief port may allow fluid to escape the inflation device prior to achieving the target pressure and not maintaining the desired target level of pressure. The Example relief port location was found to ensure the vent hole remaining above the o-ring on the head of the indicator to allow the indicator properly functioning to the alert state and allow the inflation device to pressurize a balloon in a high number of units. As seen in a bell curve 314 and Forecast values 316, a PPM total 318 of 69.27 out of 1,000,000 assemblies (PPM) will not achieve a target pressure of 11.00 ATM and would likely fail. In other words, with manufacturing tolerances, when assembled the above simulated relief port location will fall below 1.60 inches of the spring assembly length and the relief port will be fluidly exposed below the o-ring prior to achieving the target pressure 306 in 69.27 of 1,000,000 inflation devices.

Comparative Examples

Figure 6A:
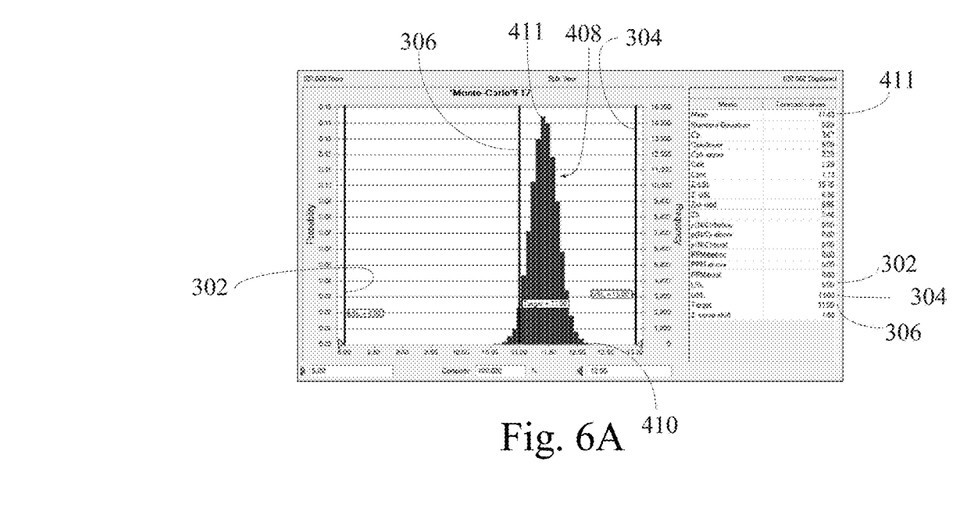
FIGS. 6A-6B are diagrammatic illustrations of a simulation of a comparative example inflation device.
Figure 6B:
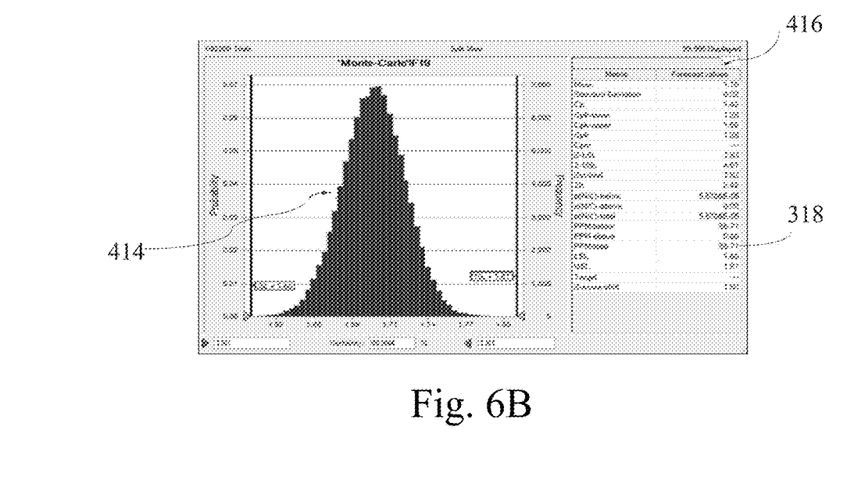

The following Monte Carlo simulations and optimizations were performed with regard to the relief port. In the Comparative Example 1 simulation as illustrated in FIGS. 6A and 6B, vented pressures of 100,000 mechanical pressure indicators were analyzed with a lower specified limit 302 of 8.00 ATM, an upper specified limit 304 of 13.00 ATM, and a target pressure 306 of 11.0 ATM. The relief port was simulated to be 1.472 inches from the trailing end of the mechanical pressure indicator housing. The spring assembly length was established between 1.600 and 1.810 inches in an unbiased state and the chamber length was established at 1.84 inches. The above noted relief port location (1.472 inches) was established through a worst case analysis and selected to ensure the vent hole remaining above the o-ring on the head of the indicator to allow the indicator properly functioning to the alert state and allow the inflation device to pressurize a balloon. A bell curve 408 of the vented pressure is illustrated in FIG. 6A. As illustrated, the maximum venting pressure 410 at the noted relief port position is about 12.4 ATM, below the 13.00 ATM upper specified limit 304. The mean pressure 411 was determined to be 11.43 ATM.

FIG. 6B illustrates the number of indicators that would likely fail, allowing fluid to escape the inflation device prior to achieving the target pressure 306 and not maintain the desired target level of pressure with the relief port at 1.472 inches from the terminal end of the housing. As seen in the Forecast values 416, 55.71 out of 1,000,000 assemblies would likely fail. In other words, with manufacturing tolerances, when assembled, the above simulated relief port location will fall below 1.60 inches of the spring assembly length and the relief port will be fluidly exposed below the o-ring prior to achieving the target pressure 306.

Figure 7:
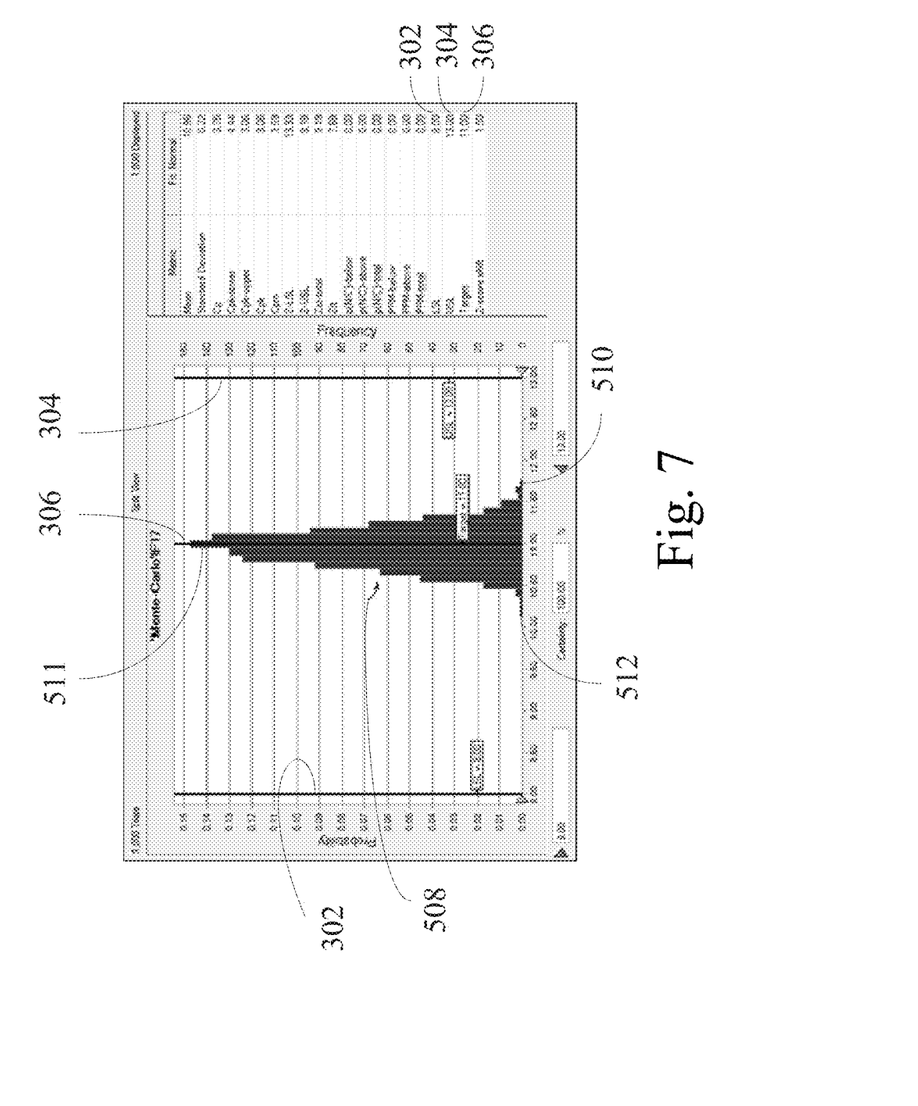
FIG. 7 is a diagrammatic illustration of a simulation of another comparative example inflation device.

The following Comparative Example 2, illustrated in FIG. 7 includes the same upper and lower limits 302, 304, target pressure 306, spring assembly length, and housing length as Comparative Example 1 illustrated in FIGS. 6A and 6B. The relief port position was optimized from that of Comparative Example 1 and positioned at 1.527 inches from the trailing end of the mechanical pressure indicator housing. A bell curve 508 of the vented pressures are illustrated in FIG. 7.

As shown in FIG. 7, a mean pressure 511 was determined to be 10.96 ATM with a minimum venting pressure 512 of the stimulation being approximately 10.2 ATM and maximum venting pressure 510 approximately 11.75 ATM.

With comparative Example 2, the number of indicators that may leak and not maintain the desired predetermined level of pressure at the relief port location 1.527 inches from trailing end and spring assembly length of 1.60 inches was simulated to be 74.82 out of 1,000,000 assemblies (i.e., will fall below 1.60 inches for the spring assembly length and fail). From this, it was determined that with the relief port located at 1.527 inches the indication distance, alert state, would be undesirably small and difficult to view.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An inflation device for selectively inflating a balloon of a surgical instrument, the device comprising:
   a syringe including a plunger slidably disposed within a barrel;
   a connector for fluidly connecting an outlet of the syringe with a surgical instrument balloon to establish a closed inflation system between the syringe and an interior of the balloon;
   a mechanical pressure indicator associated with the syringe and configured to indicate when the inflation system pressure has reached a first predetermined level, the mechanical pressure indicator including a housing defining a cavity having an indicator body slidably disposed therein, the cavity divided into a first portion and a second portion by a seal disposed on the indicator body;
   a relief port associated with the mechanical pressure indicator and configured to relieve a pressure of the inflation system when the system at least reaches the first predetermined level; and
   a cover that is assembled to the connector, the barrel of the syringe, and the mechanical pressure indicator; wherein fluid in the inflation system is expelled to within the cover from the relief port when a pressure in the inflation system is raised above the first predetermined level,
   wherein the seal is biased toward a first end of the housing by a biasing mechanism and wherein the mechanical pressure indicator is configured to transition to an alert state when a pressure acting upon a head of the indicator body overcomes a force of the biasing mechanism.

2. The device of claim 1, wherein the relief port extends fully between and interior surface and an exterior surface of a housing of the mechanical pressure indicator.

3. The device of claim 1, wherein the first portion is fluidly open to the connector at a fluid port.

4. The device of claim 1, wherein the indicator body includes an indicator head; wherein the inflation device has a first orientation when the pressure of the inflation system is below the first predetermined level in which the indicator head is entirely positioned within the cavity and the seal is distal with respect to the relief port;

wherein the inflation device has a second orientation when the pressure of the inflation system reaches the first predetermined level in which the indicator head is at least partially positioned outside of the cavity and the seal is distal with respect to the relief port;

wherein the inflation device has a third orientation when the pressure of the inflation system reaches a second predetermined level that is greater than the first predetermined level, in the third orientation the indicator head is at least partially positioned outside of the cavity and the seal is proximal with respect to the relief port.

5. The device of claim 1, wherein the first predetermined level is not less than 8.0 ATM.

6. The device of claim 1, wherein the relief port is positioned approximately 1.5 inches from a terminal end of the mechanical pressure indicator.

7. An inflation device for selectively inflating a balloon of a surgical instrument, the device comprising:
- a syringe including a plunger slidably disposed within a barrel;
- a connector for fluidly connecting an outlet of the syringe with a surgical instrument balloon to establish a closed inflation system between the syringe and an interior of the balloon;
- a mechanical pressure indicator associated with the syringe and configured to transition from a non-alert state to an alert state when a pressure of the inflation system has reached a first predetermined level, the mechanical pressure indicator including a seal; and
- a relief port associated with the mechanical pressure indicator and configured to relieve a pressure of the inflation system when the system at least reaches the predetermined level;
- wherein the inflation device has a first orientation when the pressure of the inflation system is below the first predetermined level in which the mechanical pressure indicator is in the non-alert state and the seal is distal with respect to the relief port;
- wherein the inflation device has a second orientation when the pressure of the inflation system reaches the first predetermined level in which the mechanical pressure indicator is in the alert state and the seal is distal with respect to the relief port;
- wherein the inflation device has a third orientation when the pressure of the inflation system reaches a second predetermined level that is greater than the first predetermined level, in the third orientation the mechanical pressure indicator is in the alert state and the seal is proximal with respect to the relief port.

8. The device of claim 7, further comprising a cover that is assembled to the connector, the barrel of the syringe, and a housing of the mechanical pressure indicator.

9. The device of claim 8, wherein fluid in the inflation system is expelled to within the cover from the relief port when a pressure in the inflation system is raised above the second predetermined level.

10. The device of claim 7, wherein the relief port is positioned along cylindrical side walls of a housing of the mechanical pressure indicator.

11. The device of claim 7, wherein the second predetermined level is not less than 8.0 ATM.

12. The device of claim 7, wherein the second predetermined level is between 10.1 to 13.0 ATM.

13. The device of claim 7, wherein the relief port is positioned approximately 1.5 inches from a terminal end of the mechanical pressure indicator.

14. The device of claim 7, wherein the seal is biased toward a first end of a housing of the mechanical pressure indicator with a biasing mechanism.

15. An inflation device for selectively inflating a balloon of a surgical instrument, the device comprising:
- a syringe including a plunger slidably disposed within a barrel;
- a connector for fluidly connecting an outlet of the syringe with a surgical instrument balloon to establish a closed inflation system between the syringe and an interior of the balloon;
- a mechanical pressure indicator associated with the syringe and configured to indicate when the inflation system pressure has reached a first predetermined level, the mechanical pressure indicator including a housing defining a cavity having an indicator body slidably disposed therein, the cavity divided into a first portion and a second portion by a seal disposed on the indicator body;
- a relief port associated with the mechanical pressure indicator and configured to relieve a pressure of the inflation system when the system at least reaches the first predetermined level; and
- a cover that is assembled to the connector, the barrel of the syringe, and the mechanical pressure indicator; wherein fluid in the inflation system is expelled to within the cover from the relief port when a pressure in the inflation system is raised above the first predetermined level,
- wherein the indicator body includes an indicator head, wherein the inflation device has a first orientation when the pressure of the inflation system is below the first predetermined level in which the indicator head is entirely positioned within the cavity and the seal is distal with respect to the relief port,
- wherein the inflation device has a second orientation when the pressure of the inflation system reaches the first predetermined level in which the indicator head is at least partially positioned outside of the cavity and the seal is distal with respect to the relief port,
- wherein the inflation device has a third orientation when the pressure of the inflation system reaches a second predetermined level that is greater than the first predetermined level, in the third orientation the indicator head is at least partially positioned outside of the cavity and the seal is proximal with respect to the relief port.

* * * * *